US011382725B2

(12) United States Patent
Haus

(10) Patent No.: US 11,382,725 B2
(45) Date of Patent: Jul. 12, 2022

(54) SCREW AND DRIVER TOOL

(71) Applicant: NOBEL BIOCARE SERVICES, AG, Zurich-Flughafen (CH)

(72) Inventor: Adrian Haus, Zurich (CH)

(73) Assignee: Nobel Biocare Services, AG, Kloten (CH)

( * ) Notice: Subject to any disclaimer, the term of this patent is extended or adjusted under 35 U.S.C. 154(b) by 0 days.

(21) Appl. No.: 15/681,216

(22) Filed: Aug. 18, 2017

(65) Prior Publication Data

US 2018/0028288 A1 Feb. 1, 2018

Related U.S. Application Data

(63) Continuation of application No. 14/126,368, filed as application No. PCT/EP2012/002826 on Jul. 5, 2012, now Pat. No. 9,763,754.

(30) Foreign Application Priority Data

Jul. 6, 2011 (GB) .................................. 1111561
Oct. 12, 2011 (GB) .................................. 1117590

(51) Int. Cl.
*A61C 8/00* (2006.01)
*F16B 23/00* (2006.01)
*A61K 6/802* (2020.01)

(52) U.S. Cl.
CPC .......... *A61C 8/0068* (2013.01); *A61C 8/0001* (2013.01); *A61C 8/008* (2013.01); *A61C 8/0013* (2013.01); *A61C 8/0089* (2013.01); *A61K 6/802* (2020.01); *F16B 23/0038* (2013.01); *F16B 23/0053* (2013.01)

(58) Field of Classification Search
CPC ..... A61C 8/008; A61C 8/0001; A61C 8/0013; A61C 8/0089; A61C 8/0069; A61C 8/0068; A61K 6/0205; F16B 23/0038; F16B 23/0053
USPC ... 433/8, 27, 72, 76, 80, 172–175, 165, 214, 433/180, 201.1, 202.141, 147, 172–175;
(Continued)

(56) References Cited

U.S. PATENT DOCUMENTS 2,397,216 A * 3/1946 Stellin ................. F16B 23/0007
411/404
3,213,719 A * 10/1965 Kloack ................. B25B 15/004
403/119

(Continued)

FOREIGN PATENT DOCUMENTS

DE   10 2009 015358 A1   9/2010
EP      0 997 111 A2      5/2000

(Continued)

OTHER PUBLICATIONS

Wikipedia.org, *Draft (engineering)*, accessed Jun. 14, 2016, available at: https://en.wikipedia.org/wiki/Draft_(engineering) in 1 page.

*Primary Examiner* — Nicholas D Lucchesi
*Assistant Examiner* — Mirayda A Aponte
(74) *Attorney, Agent, or Firm* — Knobbe, Martens, Olson & Bear, LLP

(57) ABSTRACT

The invention relates to a screw and corresponding screw driver for driving the screw into a dental implant at an angle from the longitudinal axis of the implant. The screw has a polygonal interface and the screw driver has a matching interface for driving the screw to rotate.

10 Claims, 7 Drawing Sheets

(58) Field of Classification Search
USPC .......... 411/403, 404, 407, 410, 919; 81/436, 81/460
See application file for complete search history.

(56) References Cited

U.S. PATENT DOCUMENTS

| | | | |
|---|---|---|---|
| 4,246,811 A * | 1/1981 | Bondhus | B25B 15/008 |
| | | | 81/436 |
| 4,345,899 A | 8/1982 | Vlock | |
| 4,384,812 A | 5/1983 | Miyagawa | |
| 4,459,074 A | 7/1984 | Capuano | |
| 5,284,073 A | 2/1994 | Wright | |
| 5,320,529 A | 6/1994 | Pompa | |
| 5,362,236 A | 11/1994 | Branemark | |
| 5,370,021 A | 12/1994 | Shigematsu | |
| 5,564,926 A | 10/1996 | Branemark | |
| 5,573,401 A | 11/1996 | Davidson | |
| 5,575,650 A | 11/1996 | Niznick et al. | |
| 5,743,916 A | 4/1998 | Greenberg et al. | |
| 5,752,828 A | 5/1998 | Andersson et al. | |
| 5,772,437 A | 6/1998 | Rangert et al. | |
| 5,833,463 A * | 11/1998 | Hurson | A61C 8/0012 |
| | | | 433/172 |
| 5,868,049 A | 2/1999 | Kanwal | |
| 5,967,777 A | 10/1999 | Klein et al. | |
| 5,989,025 A | 11/1999 | Conley | |
| 6,036,410 A | 3/2000 | Shun'ko | |
| 6,053,920 A | 4/2000 | Carlsson et al. | |
| 6,319,610 B1 | 11/2001 | Zimmer | |
| 6,402,449 B1 * | 6/2002 | Lin | F16B 23/0023 |
| | | | 411/403 |
| 6,561,805 B2 | 5/2003 | Kumar | |
| 6,626,911 B1 | 9/2003 | Engman et al. | |
| 6,641,395 B2 | 11/2003 | Kumar et al. | |
| 6,733,291 B1 | 5/2004 | Hurson | |
| 6,913,465 B2 | 7/2005 | Howlett et al. | |
| 6,955,258 B2 | 10/2005 | Howlett et al. | |
| 7,232,311 B1 | 6/2007 | Greggs | |
| 7,665,989 B2 | 2/2010 | Brajnovic et al. | |
| 7,846,357 B2 | 12/2010 | Johansson | |
| 7,942,668 B2 | 5/2011 | Brajnovic et al. | |
| 8,640,328 B1 | 2/2014 | Yow | |
| 9,095,377 B2 | 8/2015 | Karlsson et al. | |
| 9,763,754 B2 | 9/2017 | Haus | |
| 2003/0162149 A1 * | 8/2003 | Bjorn | A61C 8/005 |
| | | | 433/173 |
| 2005/0170311 A1 | 8/2005 | Tardieu et al. | |
| 2005/0214714 A1 | 9/2005 | Wohrle | |
| 2005/0277090 A1 | 12/2005 | Anderson et al. | |
| 2006/0149264 A1 | 7/2006 | Castaneda | |
| 2007/0005070 A1 | 1/2007 | Kay | |
| 2007/0248935 A1 | 10/2007 | Danger et al. | |
| 2008/0050698 A1 | 2/2008 | Carter | |
| 2008/0261176 A1 | 10/2008 | Hurson | |
| 2009/0053674 A1 | 2/2009 | Danger | |
| 2009/0202962 A1 * | 8/2009 | Xam-Mar Mangrane | |
| | | | A61C 8/005 |
| | | | 433/173 |
| 2009/0267251 A1 | 10/2009 | Johansson | |
| 2009/0325122 A1 | 12/2009 | Brajnovic et al. | |
| 2010/0009314 A1 | 1/2010 | Tardieu et al. | |
| 2010/0112517 A1 | 5/2010 | Chen | |
| 2010/0167240 A1 * | 7/2010 | Benzon | A61C 8/0089 |
| | | | 433/174 |
| 2010/0209877 A1 * | 8/2010 | Hogan | A61C 8/0001 |
| | | | 433/214 |
| 2010/0285427 A1 | 11/2010 | Hung | |
| 2010/0291509 A1 | 11/2010 | Berggren et al. | |
| 2010/0312248 A1 | 12/2010 | Karlsson et al. | |
| 2011/0229853 A1 | 9/2011 | Chen | |
| 2012/0099944 A1 * | 4/2012 | Kageyama | B25B 15/005 |
| | | | 411/403 |
| 2012/0135373 A1 | 5/2012 | Cheng et al. | |
| 2014/0178836 A1 | 6/2014 | Haus et al. | |
| 2014/0186797 A1 | 7/2014 | Haus | |
| 2015/0238289 A1 | 8/2015 | Wouters et al. | |
| 2015/0238290 A1 | 8/2015 | Wouters et al. | |
| 2015/0245890 A1 | 9/2015 | Wouters et al. | |
| 2015/0342617 A1 | 12/2015 | Kunz et al. | |

FOREIGN PATENT DOCUMENTS

| | | | |
|---|---|---|---|
| EP | 1039151 | 9/2000 | |
| EP | 1 323 394 A1 | 7/2003 | |
| EP | 2 174 616 A1 | 4/2010 | |
| GB | 191417073 | 2/1916 | |
| GB | 575978 | 4/1944 | |
| GB | 2 154 487 A | 9/1985 | |
| JP | WO 2010150369 A1 * | 12/2010 | ........... B25B 15/005 |
| WO | WO 00/27300 | 5/2000 | |
| WO | WO 2003/003937 | 1/2003 | |
| WO | WO 2005/030081 A1 | 4/2005 | |
| WO | WO 2008/064350 | 5/2008 | |
| WO | WO 2010/054169 A1 | 5/2010 | |
| WO | WO 2011/023750 A2 | 3/2011 | |
| WO | WO 2013/004386 | 1/2013 | |
| WO | WO 2014/095033 | 6/2014 | |
| WO | WO 2014/095034 | 6/2014 | |

* cited by examiner

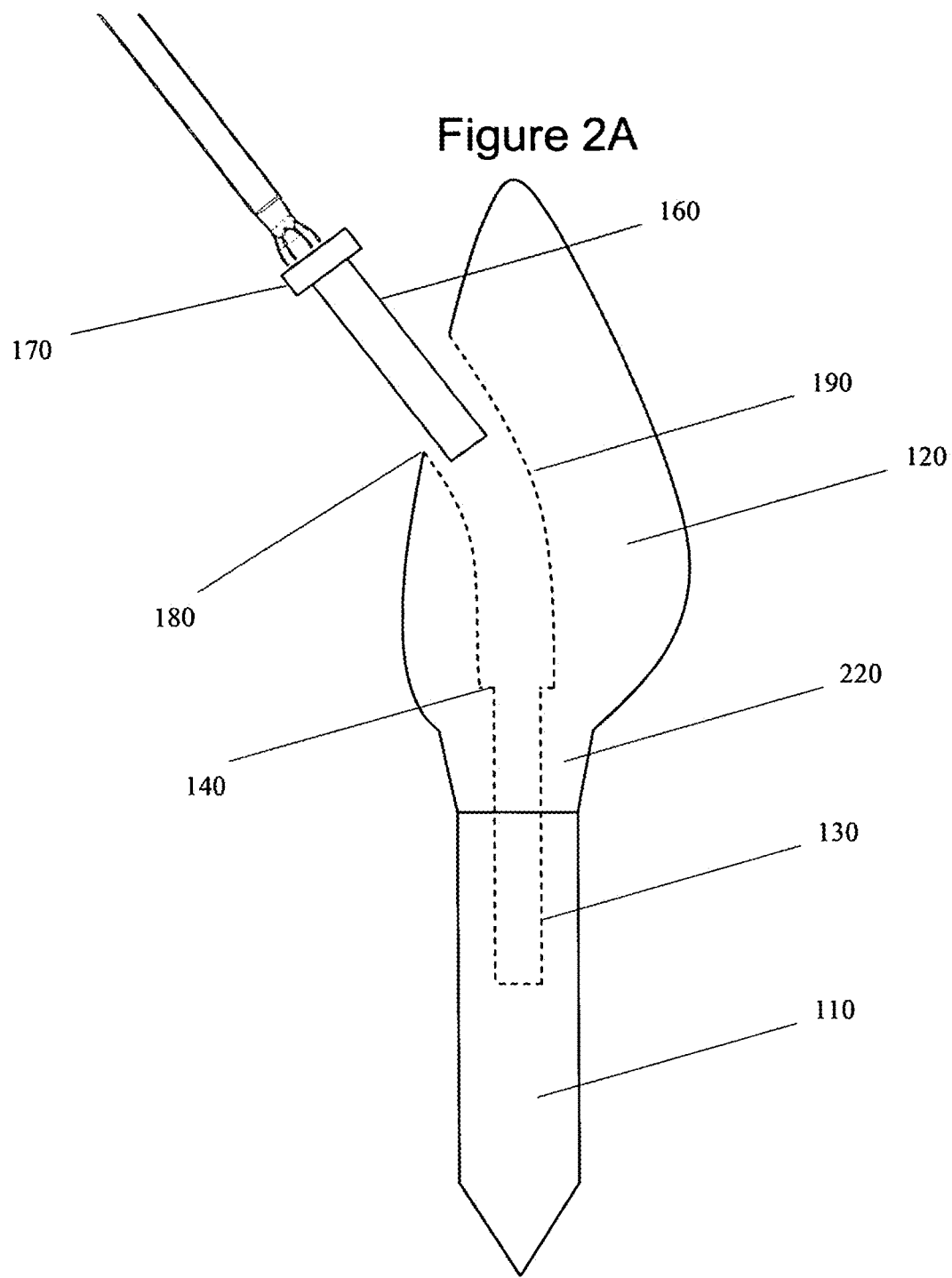

US 11,382,725 B2

SCREW AND DRIVER TOOL

PRIORITY INFORMATION

This application is a continuation of U.S. application Ser. No. 14/126,368 having a § 371(c)(1), (2), (4) date of Jan. 10, 2014, which is a national stage application under 35 U.S.C. § 371 of PCT Application No. PCT/EP2012/002826, filed on Jul. 5, 2012, which published in English as WO 2013/004386 on Jan. 10, 2013, and which claims priority benefit of GB Patent Application No. 1111561.5, filed on Jul. 6, 2011, and GB Patent Application No. 1117590.8, filed on Oct. 12, 2011.

BACKGROUND

Field of the Invention

The present invention relates to methods and apparatus for fixing dental components to dental implants in a patient's jawbone. More specifically, the invention relates to the manipulation of screws into dental components with corresponding screw channels in order to secure the dental component to the dental implant.

Description of the Related Art

FIG. 1 shows an arrangement for a prosthetic single tooth replacement having angulated screw channels. Dental implant 110 comprises screw channel 130 having an inner thread configured to match the thread of screw 160 such that screw 160 can be fastened to the implant. Prosthesis 120 is fixed to the dental implant by means of screw 160. The prosthesis passes through the gum tissue to dental implant 110. The prosthesis has a screw channel 190 through which screw 160 is inserted. Screw channel 190 has a screw channel exit 180 and screw seat 140 at the base of the prosthesis, upon which the head 170 of the screw 160 is seated when the prosthesis is fastened to the implant with the screw. According to the present invention, the axis of screw channel 190 (i.e. the line described by the radial centre point of the channel at any point) does not follow the axis of channel 130. In fact, screw channel 190 may be mostly straight but orientated at a different angle to channel 130. Alternatively, the axis of screw channel 190 may be curving or S-shaped. As a result, the axis of screw channel 190 at the channel exit 180 does not match the axis of channel 130 or the axis of screw seat 140.

The problem arising from this arrangement is that of how to insert the screw through the angulated screw channel and, once the screw is engaged with the dental implant, how to drive the screw to rotate using a driver angled at a significant angle from the longitudinal axis of the screw.

What is needed is a way of interfacing the screw and a driver tool in a manner which allows the screw to be manipulated during insertion into the prosthesis and driven to rotate from an angle to the longitudinal axis of the screw.

US 2010167240 describes a driver tool for driving a screw to rotate from an angle from the axis of the screw. A ball-headed driver is described, wherein the ball shape of the driver head apparently provides an interface between the driver and the screw, even where the driver tool is presented at an angle from the axis of the screw.

SUMMARY

According to a first aspect of the invention, there is provided a screw for a dental application (in other words, a dental screw), the screw having a coronal end and an apical end and comprising a bore running from the coronal end of the screw along a portion of the screw towards the apical end of the screw, a first number of equally spaced recesses arranged circumferentially around an inside surface of the bore, each recess running a length from the coronal end of the bore towards the apical end of the bore. The length of each recess is angled relative to the longitudinal axis of the screw such that the recess is further from the longitudinal axis of the screw at a point parallel with the coronal end of the bore than at a point below the coronal end of the bore. Each pair of adjacent recesses is connected by a contact surface on the inside surface of the bore, each contact surface running a length from the coronal end of the bore towards the apical end of the screw. Each contact surface is angled away from the longitudinal axis of the screw such that the surface is further from the longitudinal axis of the screw at a point parallel with the coronal end of the bore than at a point below the coronal end of the bore.

At least a portion of the inside surface of the bore comprises a layer of Titanium Nitride. The apical end of the bore may be conical, having a widest point at the apical end of the recesses. In one embodiment, the screw is adapted to fasten a dental component to a dental implant. In another embodiment, the screw (itself) is a dental component directly attachable to a dental implant, wherein the dental component may be selected from the group comprising: a cover screw, a healing abutment, an impression coping, etc.

According to another aspect of the invention, there is provided a driver for driving a screw for fastening a dental component to a dental implant, the driver comprising a driver head having an apical and coronal end, the driver head comprising of at least a first and second portion having a polygonal cross-section in a radial plane of the longitudinal axis of the driver, a first portion having a substantially rounded cross-section in the axial plane of the longitudinal axis of the driver, a second portion connected apically relative to the first portion, the second portion having a substantially triangular shape tapered towards the apical end of the driver head in the axial plane of the longitudinal axis of the driver.

The driver head may comprise a tip portion at the apical end of the driver head having a polygonal cross-section in a radial plane of the longitudinal axis of the driver and a curved apical end. At least a portion of the surface of the driver head may comprise a layer of Titanium Nitride.

According to yet another aspect of the invention, a method of fastening a dental component to a dental implant comprising the steps of, inserting the driver head of a driver described above into the bore of any of the screws described above such that the edges of the driver head defined by the polygonal cross-section fit within the recesses of the screw, applying sufficient force to the driver so that the driver head grips the screw by means of a carry function, manipulating the screw through a screw channel of the dental component using the carry function until the screw is received by a threaded bore in the dental implant, driving the screw to rotate using the driver, such that the edges of the driver head defined by the polygonal cross section of the portions of the driver head smoothly convey rotational force to the screw regardless of the angle of the longitudinal axis of the driver relative to the longitudinal axis of the screw.

BRIEF DESCRIPTION OF THE DRAWINGS

Aspects of the present invention will now be described by way of example with reference to the accompanying drawing. In the drawings:

FIG. 2A shows the angle of the driver (not shown to scale) from the longitudinal axis of the screw during the process of inserting a screw into an prosthesis of FIG. 1.

DETAILED DESCRIPTION

Figure 1:
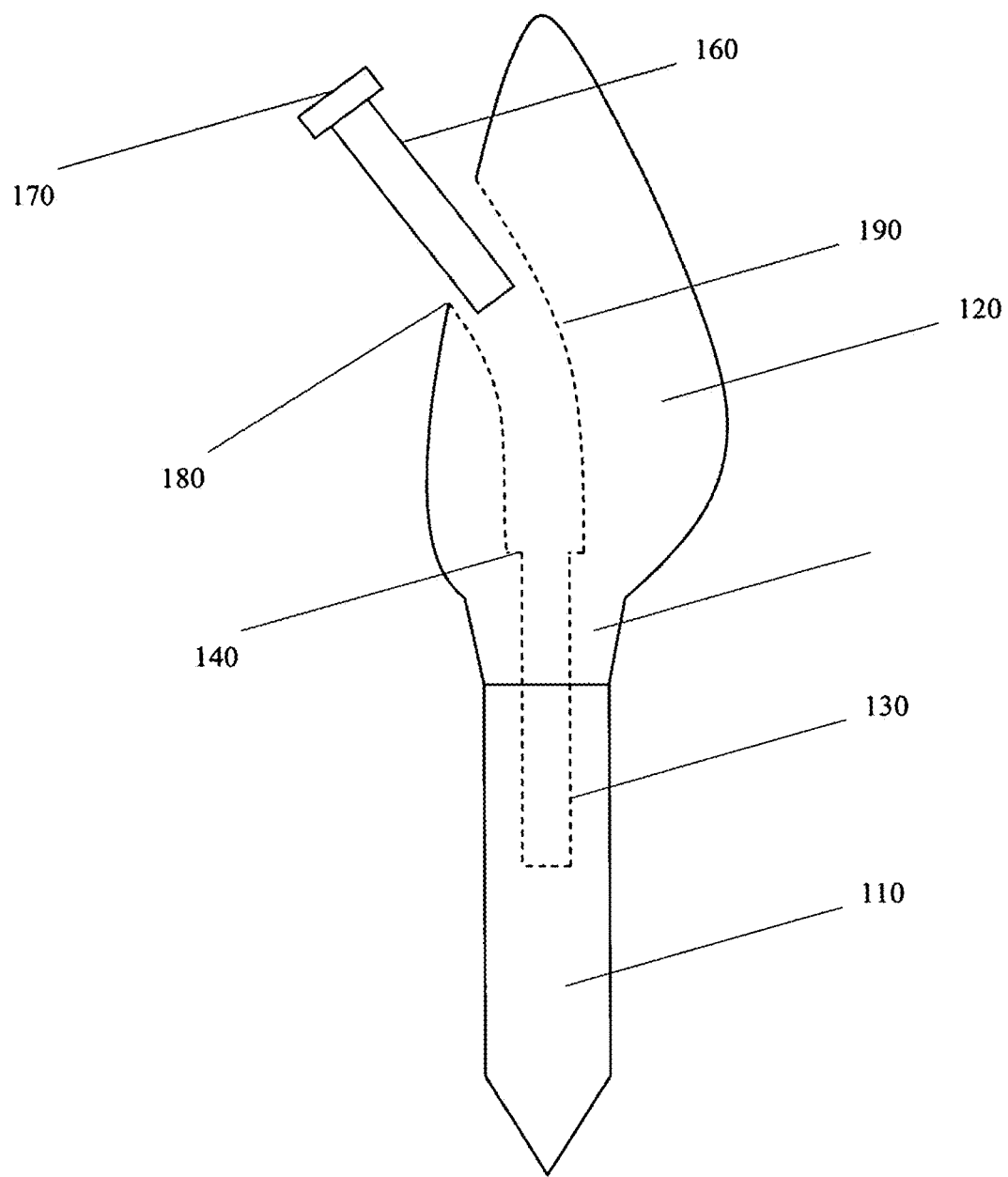
FIG. 1 shows a prosthesis having angulated screw channel and corresponding screw.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Screw

The present invention provides a method and apparatus for inserting a screw into a dental component having an angulated screw channel and securing the screw into a dental implant, thereby fixing the dental component to the dental implant.

Figures 3A, 3B:
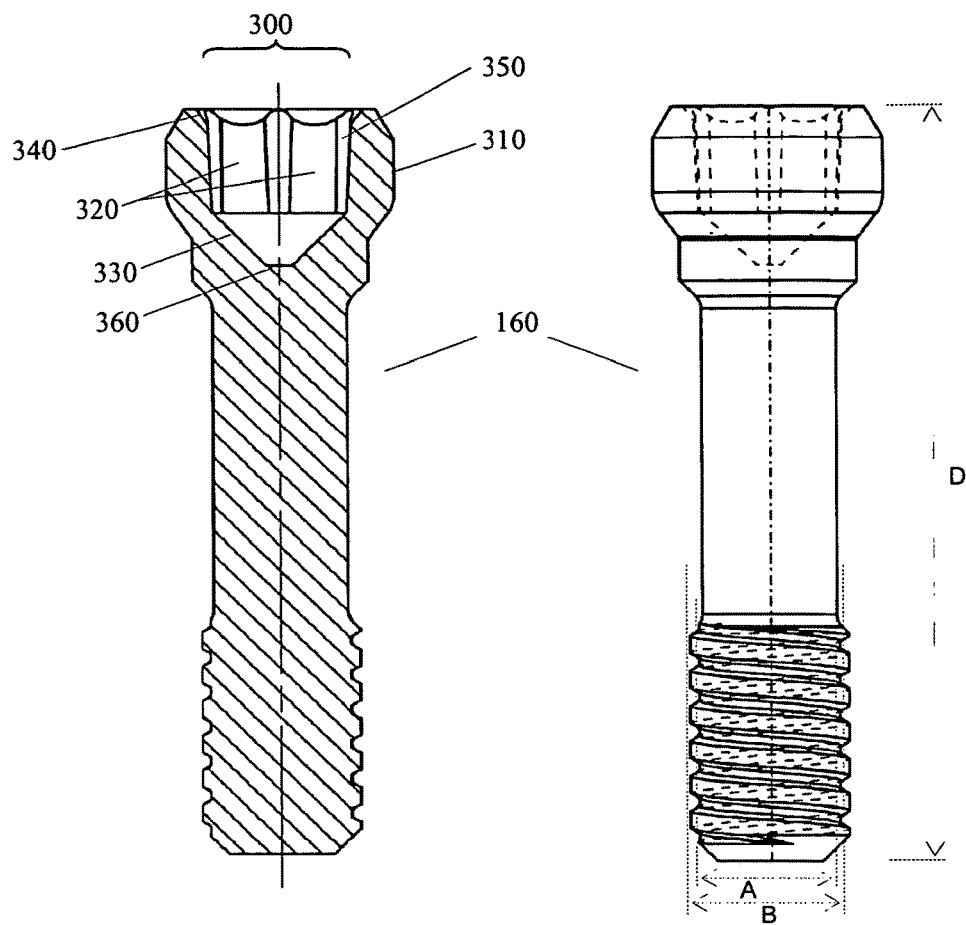
FIG. 3A shows an embodiment of the screw according to the invention.
FIG. 3B shows an embodiment of the screw according to the invention.
Figures 3C, 3D:
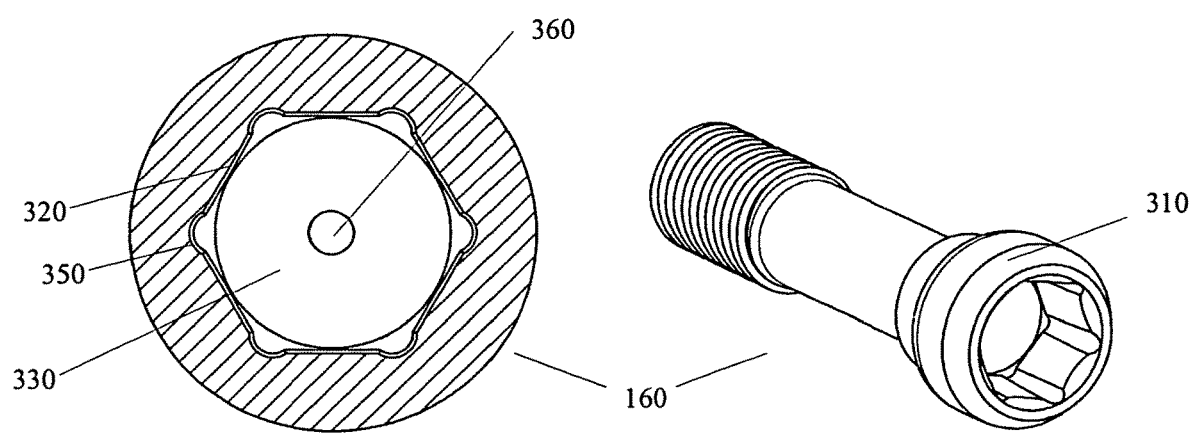
FIG. 3C shows an embodiment of the screw according to the invention.
FIG. 3D shows an embodiment of the screw according to the invention.

A screw having a screw interface according to the preferred embodiment of the present invention is shown in FIGS. 3A to 3D. Screw 160 comprises screw head 310 having screw interface 300. The screw interface 300 comprises a bore in the head of the screw with a polygonal internal shape configured to co-operate with screw driver head 400, described later in the specification. As shown in FIG. 3A, screw interface 300 comprises tapered inner walls 320, conical section 330, chamfered or rounded interface edges 340 and recesses 350.

In the preferred embodiment, screw interface 300 comprises six equally spaced recesses 350 arranged circumferentially on the inside surface of the screw interface. An equivalent screw head with greater or fewer than six recesses is also envisaged. Each recess runs from the top surface of the screw head at a small angle (e.g. 2.5 degrees) inwards from the longitudinal axis of the screw towards conical section 330. In between the recesses are flat tapered surfaces 320, tapered outwardly towards the mouth of the screw interface. As a consequence, the internal surfaces 350 and 320 describe a slightly conical internal space such that the largest diameter at the mouth of the screw interface is greater than the largest diameter at the point where the tapered surfaces 320 meet the conical section below. In one embodiment, the tapered surfaces 320 are angled 2.5° from the longitudinal axis of the screw.

Conical section 330 comprises the bottom portion of the screw interface 300. At the widest point of the cone, conical section 330 meets the recesses 350 and tapered inner surfaces 320. The cone shape of section 330 then narrows to a truncated head 360 at the internal end of the screw interface. Cone 330 provides extra support to screw head edges 310 when the screw is inserted tightly into a screw seat. Whereas a flat lower surface (e.g. truncated portion 360 being the width of the interface) might allow the edges to plastically deform inwards as the screw was screwed tightly into a screw seat, conical shape 330 provides greater support to edges 310.

The mouth of the screw interface 300 comprises six chamfered or rounded edges 340 connecting the top surface of screw head 310 and tapered inner surfaces 320.

Figure 6A:
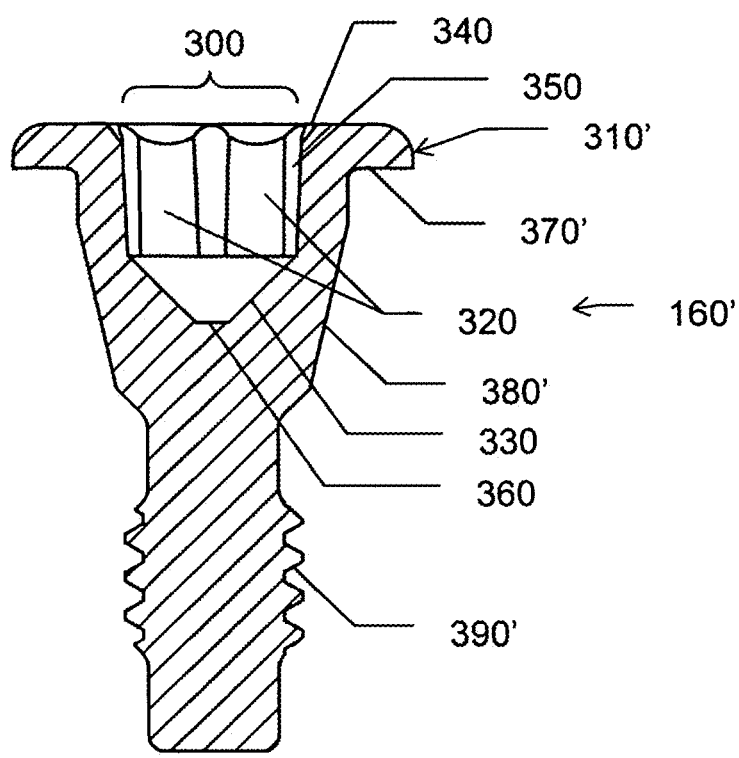
FIG. 6A shows an embodiment of a cover screw according to the invention.
Figure 6B:
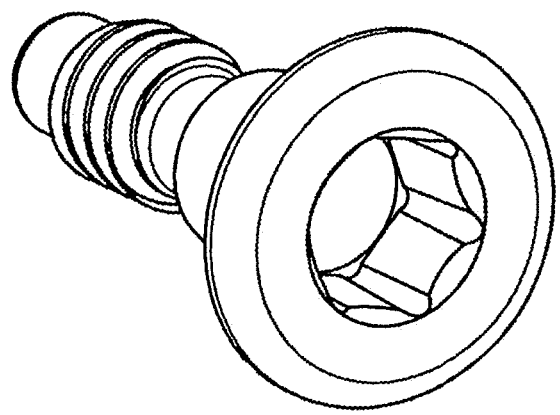
FIG. 6B shows an embodiment of a cover screw according to the invention.

FIG. 6A is cross-sectional side view, and FIG. 6B is perspective view, of an embodiment of a cover screw 160' according to the invention. The cover screw 160' is generally adapted to completely cover the top (i.e. the coronal end) of a dental implant, for example the dental implant 110.

The cover screw 160' comprises a screw head 310'. The screw head 310' comprises a flat circumferential apical surface 370'. The surface 370' is orthogonal to the longitudinal axis of the cover screw 160'. The surface 370' is adapted to abut against and cover the top of the dental implant.

The screw head 310' further comprises a screw interface 300. The screw interface 300 is of the same type as the screw interface of the screw 160 described in relation to FIGS. 3A to 3D. Therefore, the same driver or tool may be used to manipulate both the screw 160 and the cover screw 160'. The description of the screw interface 300 will not be repeated here.

Apically of the surface 370', the cover screw 160' comprises a conical section 380', which narrows toward the apical end of the cover screw 160'. The conical section 380' is adapted to abut against a corresponding conical section of the dental implant (internal conical connection), when the cover screw 160' is screwed into the implant.

Apically of the conical section 380', the cover screw 160' comprises an externally threaded portion 390' for engagement with a corresponding internally threaded portion of the dental implant, so that the cover screw 160' can be secured to the dental implant.

The screw interface 300 may also be applied to other dental components than cover screws, such as healing abutments, impression copings, etc.

Driver

Figure 4A:
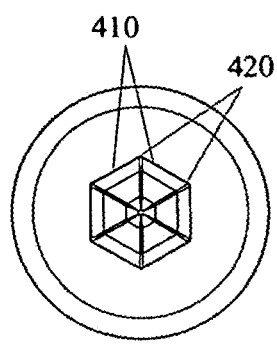
FIG. 4A shows an embodiment of the screw driver according to the invention.
Figure 4B:
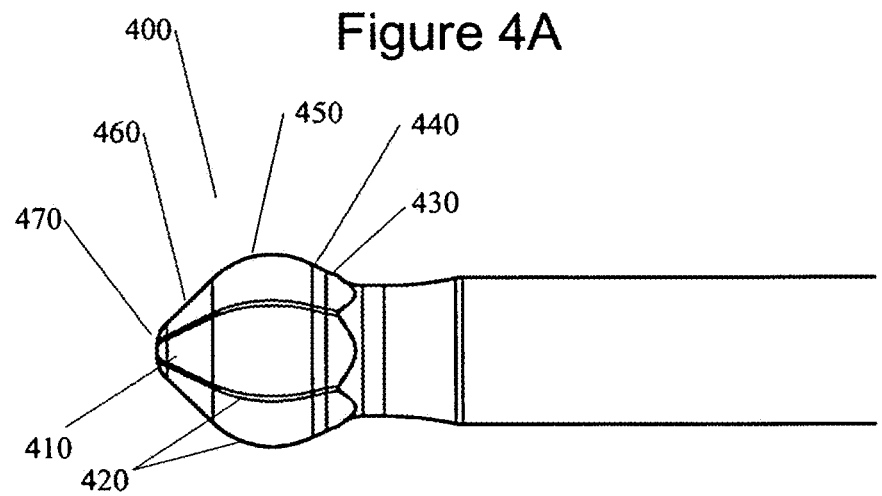
FIG. 4B shows an embodiment of the screw driver according to the invention.
Figure 4C:
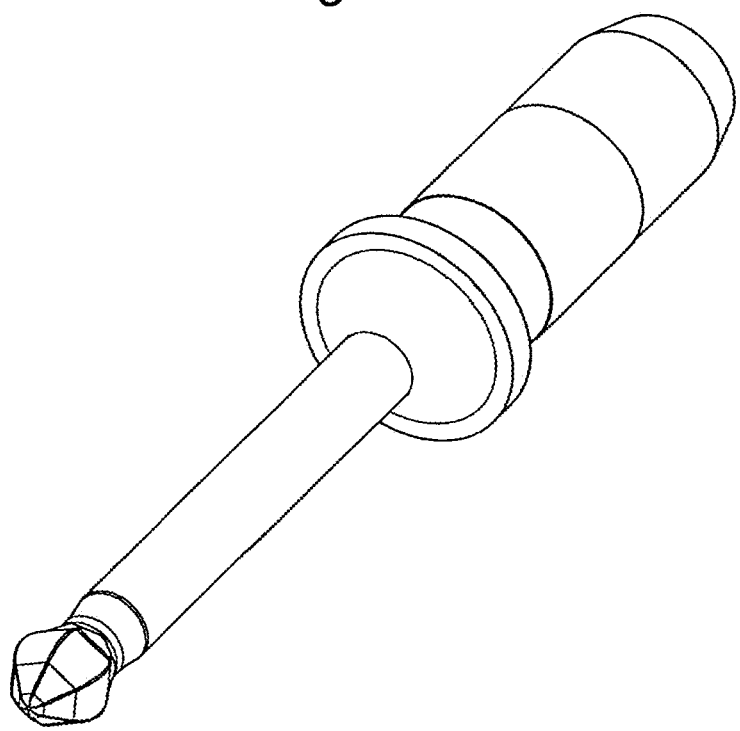
FIG. 4C shows an embodiment of the screw driver according to the invention.

According to the preferred embodiment of the invention shown in FIGS. 4A-4C, the screw driver head 400 comprises a polygonal shape in the radial plane (i.e. the plane normal to the longitudinal axis of the driver) and a ball shape in the axial plane.

In particular, the preferred embodiment of the driver head 400 has a polygonal cross section as shown in FIG. 4A. In the preferred embodiment, the polygonal cross section has six sides. However, an equivalent driver head with greater or fewer than six sides (corresponding to the number of recesses in the screw interface) is envisaged. The sides of the polygons form surfaces 410, spanning between edges 420

In FIG. 4B, the screw driver head is shown in a side perspective. In order to describe the driver head, it is divided up into portions 430, 440, 450, 460, and 470.

Edges 410 of apical end portion 470 describe a circular curve where all the edges 410 meet. The circular curve of the edges at apical end portion 470 describe a rounded head in the axial plane.

Edges 410 of portion 460 describe a straight line, such that the portion 460 comprises the shape of a truncated polygonal pyramid, truncated towards apical end 470 such that the surfaces of portion 460 smoothly meet the surfaces of portion 470.

Edges 410 of apical end portion 450 describe a circular curve connecting the edges of portion 460 to portion 440. The circular curve is that which give portion 450 a truncated ball shape in the axial plane.

Edges 410 of portion 440 describe a straight line, such that the portion 460 comprises the shape of a truncated polygonal pyramid, narrowing away from apical end 470 such that the surfaces of portion 450 smoothly meets the surfaces of portion 430.

Portion 430 is where surfaces 420 meet the cylindrical shaft of the driver tool.

Co-Operation Between the Driver Head and the Screw Interface

Figures 5A, 5B, 5C:
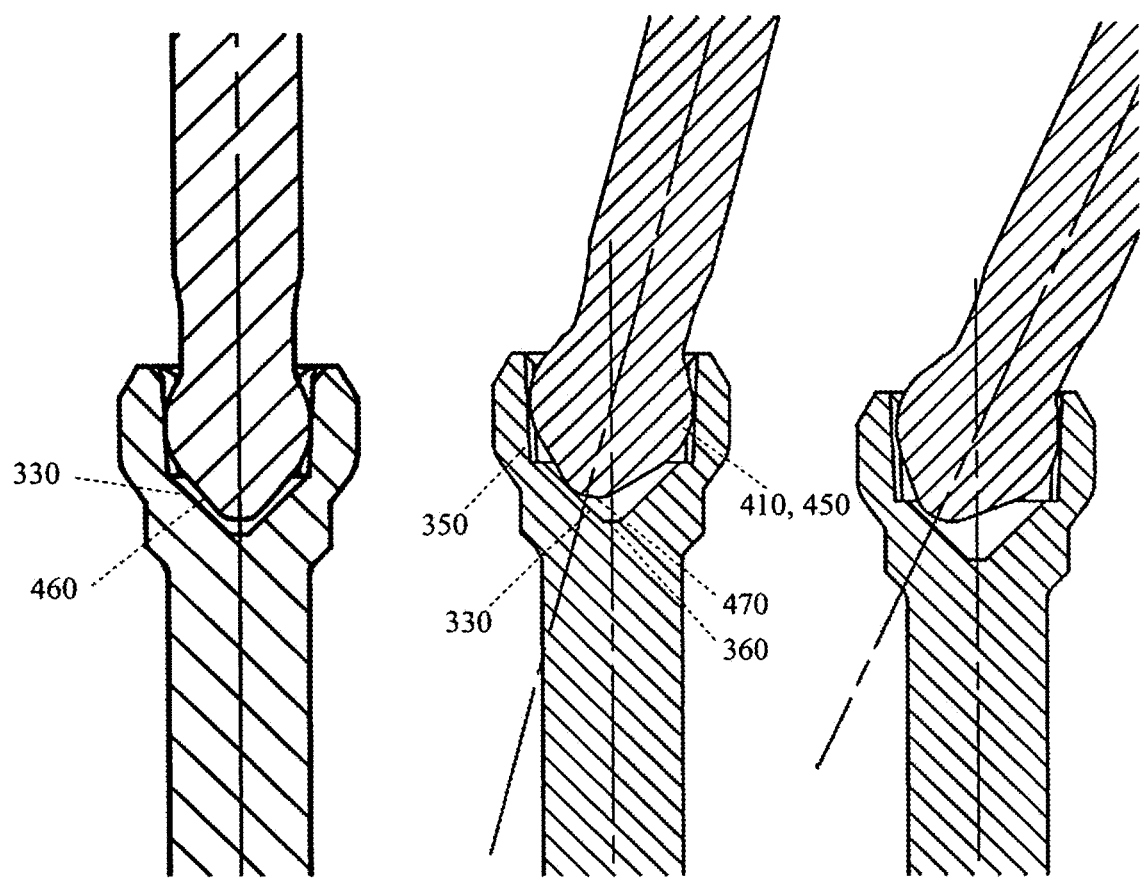
FIG. 5A shows the screw in co-operation with the screw driver head.
FIG. 5B shows the screw in co-operation with the screw driver head.
FIG. 5C shows the screw in co-operation with the screw driver head.

As shown in FIGS. 5A to 5C, the features of the driver head and corresponding screw interface are configured to allow the driver head to be inserted into the screw interface and for the screw to be driven to rotate by the driver at an angle from the longitudinal axis of the screw.

Upon initial insertion of the driver head into the screw interface, chamfered (or rounded) edges 340 of the mouth of the screw interface guide the tip of the driver head into the bore of the screw. This makes the process of loading the driver head into the screw more simple and require less precise spatial co-ordination from the person manipulating the driver/screw.

The driver head is then rotated until edges 410 align with recesses 330. At this point, edges 410 will fit into recesses 330 and the driver head will obtain rotational grip with the screw head. The recesses allow the driver head to be smoothly rotated at an angle from the longitudinal axis of the screw without a locking collision between the surfaces of the driver head and the screw interface causing the driver head to become rotationally fixed to the screw.

As shown in FIG. 5A, if the screw head is inserted into the screw interface at an angle matching, or close to, the longitudinal axis of the screw, the conical portion 460 will rest against internal cone 330 to provide a comfortable fit and the driver may be driven to rotate the screw.

If, as shown in FIGS. 5B and 5C, the screw head is inserted into the screw interface at a significant angle from the longitudinal axis of the screw (i.e. greater than 5 degrees), rounded apical end 470 meets internal cone 330 at a point above the truncated end 360 of the internal cone. This prevents the screw head from entering the screw interface as deeply as when the screw head is inserted into the screw interface at an angle close to the longitudinal axis of the screw. At the same time, rounded edges 410 of portion 450 fit with recesses 350. In the preferred embodiment, the gradient angle of the internal cone 330 is chosen to ensure that depth to which the driver head enters the screw head is dependent on the angle from the longitudinal axis of the screw that the driver head is inserted. By controlling the depth to which the screw head enters the screw interface, rounded edges 410 of portion 450 can be controlled to contact recesses 350 within an optimal range of the length of recesses 350, i.e. not too close to the mouth of the screw interface such that the driver head slips out of rotational grip with the screw, and not so close to the internal end of the screw interface that the rounded portion 450 contacts internal conical portion 330 and introduces extra friction or forces the screw head back out of the screw interface. In one embodiment, the range of optimal contact for rounded portion 450 on recesses 350 is between points describing 25% and 75% of the length of the recess. By ensuring that a section of the rounded edges contacts the conical portion 330 within this range, an optimal play between the screw and the driver is achieved to allow angulated rotation of screw. Once the driver head is moved to rotate, the rounded aspect of portion 450 in recesses 350 allows the screw to be rotated at an angle from the longitudinal axis from the driver.

Surface 460 of the driver also provides extra contact surface during the driving process. For a rounded driver head, each edge in the recess would curve out of the recess after the point at which the edge and the recess surface were contacting. The straight surface does not curve out of the recess and provides some degree of surface contact until the end of the recess.

Figure 2B:
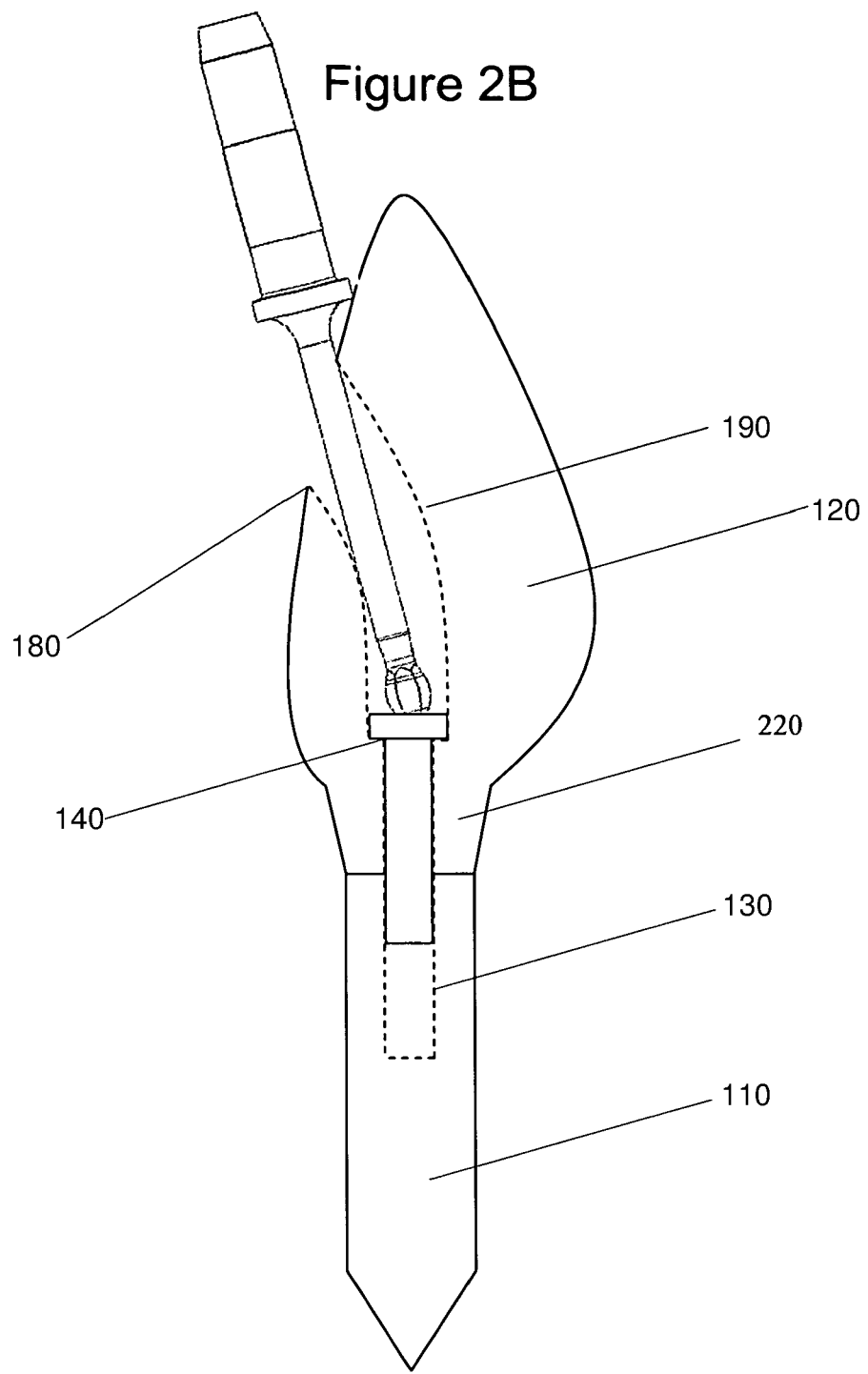
FIG. 2B shows the angle of the driver (not shown to scale) from the longitudinal axis of the screw during the process of inserting a screw into an prosthesis of FIG. 1.

In the preferred embodiment of the invention, the slight angling of the recesses 350 and the surfaces 320 from the longitudinal axis of the screw provides a carry function for the driver head. The slight angle means that, if the screw head is pushed into the screw interface with a certain force, edges 450 are pushed into recesses 350 with an increasingly tighter fit. Once a certain point is reached, the surfaces of the driver head are pressed against the inner surface of the screw interface so tightly that the resultant friction fit allows the screw to be picked up by the driver head and carried without any support for the screw. This is called a carry function and can be vital for simplifying the process of installing the screw in a dental implant. In the preferred embodiment, the configuration of the preferred driver head and interface allows this carry function to exist even when the driver head is inserted at an angle from the longitudinal axis of the screw. This is particularly advantageous when inserting a screw into an angulated screw channel (as shown in FIGS. 2A and 2B). Furthermore, the configuration of the preferred driver head and interface allows the contact position of rounded portion 450 to be controlled to be within the optimal range, and so the optimal amount of friction to achieve the carry function can also be controlled.

In a preferred embodiment of the invention, either or both of the surfaces of the driver head or the internal surface of the screw interface are applied with a coating, such as Titanium Nitride, which increases the friction between the components. This provides an enhanced carry function between the driver head and the screw interface and reduces the risk of the screw being dropped.

In an alternative embodiment of the invention, the number of recesses in the screw interface is greater than six. An increased number of recesses provides a smoother action between the co-operating surfaces of the screw interface during rotation of the screw by the driver head.

What is claimed is:

1. A screw for dental application, the screw comprising a coronal end and an apical end and comprising:
   a bore running from the coronal end of the screw along a portion of the screw towards the apical end of the screw, a first number of equally spaced recesses arranged circumferentially around an inside surface of the bore, each recess running a length from the coronal end of the bore towards the apical end of the bore,
wherein the length of each recess is angled relative to the longitudinal axis of the screw by a first angle such that the recess is further from the longitudinal axis of the screw at a point parallel with the coronal end of the bore than at a point below the coronal end of the bore,
wherein each pair of adjacent recesses are connected by a contact surface on the inside surface of the bore, each contact surface running a length from the coronal end of the bore towards the apical end of the screw,
wherein each contact surface is flat and planar and angled away from the longitudinal axis of the screw such that the surface is further from the longitudinal axis of the screw at a point parallel with the coronal end of the bore than at a point below the coronal end of the bore,
wherein the apical end of the bore comprises a conical section that is angled relative to the longitudinal axis by a second angle, the second angle being greater than the first angle,
wherein a coronal edge of each of the contact surfaces is rounded, and
wherein the screw is configured for fastening a dental component to a further dental component.

2. The screw of claim 1, wherein at least a portion of the inside surface of the bore comprises a layer of Titanium Nitride.

3. The screw of claim 1, wherein the apical end of the bore is conical, comprising a widest point at the apical end of the recesses.

4. The screw of claim 1, wherein the screw is adapted to fasten a dental component to a dental implant.

5. The screw of claim 1, wherein the screw is a dental component directly attachable to a dental implant.

6. The screw of claim 5, wherein the dental component is selected from the group comprising: a cover screw, a healing abutment, and an impression coping.

7. A driver for driving a screw for fastening a dental component to a dental implant,
the driver comprising a driver head comprising an apical and coronal end,
the driver head comprising at least a first, a second, and a third portion, the first and second portion comprising a polygonal cross-section in a radial plane, the radial plane being perpendicular to the longitudinal axis of the driver, wherein a plurality of edges of the first portion and the second portion are continuous in the direction of the longitudinal axis of the driver; the first portion comprising a convex, rounded cross-section in an axial plane parallel to the longitudinal axis of the driver, the first portion curving radially inward towards the longitudinal axis of the driver head at apical and coronal ends of the first portion; the second portion connected apically relative to the first portion, the second portion comprising a triangular shape tapered towards the apical end of the driver head in the axial plane; the third portion connected apically relative to the second portion, the third portion forming a continuously curved apical tip of the driver head, the third portion describing a substantially circular curve where all of a plurality of edges of the second portion meet the third portion; wherein the axial length of the third portion in the axial plane is substantially less than the axial length of the second portion in the axial plane, and wherein in the axial plane, the second portion gradually transitions radially in all directions around the longitudinal axis to the third portion.

8. The driver of claim 7, wherein the driver head comprises a tip portion at the apical end of the driver head comprising a polygonal cross-section in a radial plane of the longitudinal axis of the driver and a curved apical end.

9. The driver of claim 7, wherein at least a portion of the surface of the driver head comprises a layer of Titanium Nitride.

10. A method of fastening a dental component to a dental implant, the method comprising:
inserting the driver head of a driver into the bore of a screw such that the edges of the driver head defined by a polygonal cross-section fit within the recesses of the screw,
the driver comprising a driver head comprising an apical and coronal end, the driver head comprising of at least a first and second portion comprising a polygonal cross-section in a radial plane of the longitudinal axis of the driver, the first portion comprising a substantially rounded cross-section in the axial plane of the longitudinal axis of the driver, the second portion connected apically relative to the first portion, the second portion comprising a substantially triangular shape tapered towards the apical end of the driver head in the axial plane of the longitudinal axis of the driver, the driver further comprising a coronal portion connected coronally to the first portion, the coronal portion comprising a triangular shape tapered towards the coronal end of the driver in the axial plane, and
the screw comprising a coronal end and an apical end, the screw comprising:
a bore running from the coronal end of the screw along a portion of the screw towards the apical end of the screw,
a first number of equally spaced recesses arranged circumferentially around an inside surface of the bore, each recess running a length from the coronal end of the bore towards the apical end of the bore,
wherein the length of each recess is angled relative to the longitudinal axis of the screw such that the recess is further from the longitudinal axis of the screw at a point parallel with the coronal end of the bore than at a point below the coronal end of the bore,
wherein each pair of adjacent recesses are connected by a contact surface on the inside surface of the bore, each contact surface running a length from the coronal end of the bore towards the apical end of the screw, and
wherein each contact surface is flat and planar and angled away from the longitudinal axis of the screw such that the surface is further from the longitudinal axis of the screw at a point parallel with the coronal end of the bore than at a point below the coronal end of the bore,
wherein a coronal edge of each contact surface is rounded, and
wherein the screw is configured for fastening a dental component to a further dental component,
applying sufficient force to the driver so that the driver head grips the screw by means of a carry function, manipulating the screw through a screw channel of the dental component using the carry function until the screw is received by a threaded bore in the dental implant, driving the screw to rotate using the driver, such that the edges of the driver head defined by the polygonal cross section of the portions of the driver head smoothly convey rotational force to the screw regardless of the angle of the longitudinal axis of the driver relative to the longitudinal axis of the screw.

* * * * *